United States Patent
Schweiger

(10) Patent No.: US 10,130,448 B2
(45) Date of Patent: Nov. 20, 2018

(54) DENTAL RESTORATION

(71) Applicant: Ivoclar Vivadent AG, Schaan (LI)

(72) Inventor: Josef Schweiger, Bergen (DE)

(73) Assignee: Ivoclar Vivadent AG, Schaan (LI)

( * ) Notice: Subject to any disclaimer, the term of this patent is extended or adjusted under 35 U.S.C. 154(b) by 95 days.

(21) Appl. No.: 14/785,190

(22) PCT Filed: Sep. 3, 2014

(86) PCT No.: PCT/EP2014/068761
§ 371 (c)(1),
(2) Date: Oct. 16, 2015

(87) PCT Pub. No.: WO2015/032831
PCT Pub. Date: Mar. 12, 2015

(65) Prior Publication Data
US 2016/0081772 A1    Mar. 24, 2016

(30) Foreign Application Priority Data
Sep. 3, 2013 (DE) .......... 10 2013 014 660

(51) Int. Cl.
*A61C 8/00* (2006.01)
*A61C 13/00* (2006.01)
(Continued)

(52) U.S. Cl.
CPC .......... *A61C 8/0068* (2013.01); *A61C 8/0012* (2013.01); *A61C 8/0048* (2013.01);
(Continued)

(58) Field of Classification Search
CPC ... A61C 8/0068; A61C 8/0012; A61C 8/0048; A61C 8/0089; A61C 13/0004;
(Continued)

(56) References Cited

U.S. PATENT DOCUMENTS 5,098,294 A * 3/1992 Lee ............ A61C 8/0018
433/169
5,580,246 A * 12/1996 Fried ............ A61C 8/0048
433/172

(Continued)

FOREIGN PATENT DOCUMENTS

EP    2289461 A1 *  3/2011  ........... A61C 8/0048
EP    2452650 A1 *  5/2012  ......... A61C 13/0018
(Continued)

*Primary Examiner* — Ralph Lewis
(74) *Attorney, Agent, or Firm* — Ann M. Knab; Thad McMurray

(57) ABSTRACT

The invention relates to a dental restoration, having a base which in particular comprises an implant (1) in combination with an abutment (4), and a supraconstruction (3) which is fixed to the base, in particular by adhesive bonding, wherein the base has a screw connection having a screw head which extends over or on the base. Said screw head connects the two parts of the base to each other so as to be fixed against rotation, and has an access channel (10, 35) for the screw, the opening of which is offset with respect to the extension of the axis of the screw in the lingual direction of the supraconstruction (3). The diameter of the access channel (10, 35) is smaller than the diameter of the screw head of the screw, and the screw can be screwed through the access channel (10, 35), i.e. can be screwed in and screwed out.

24 Claims, 9 Drawing Sheets

Figure 1:
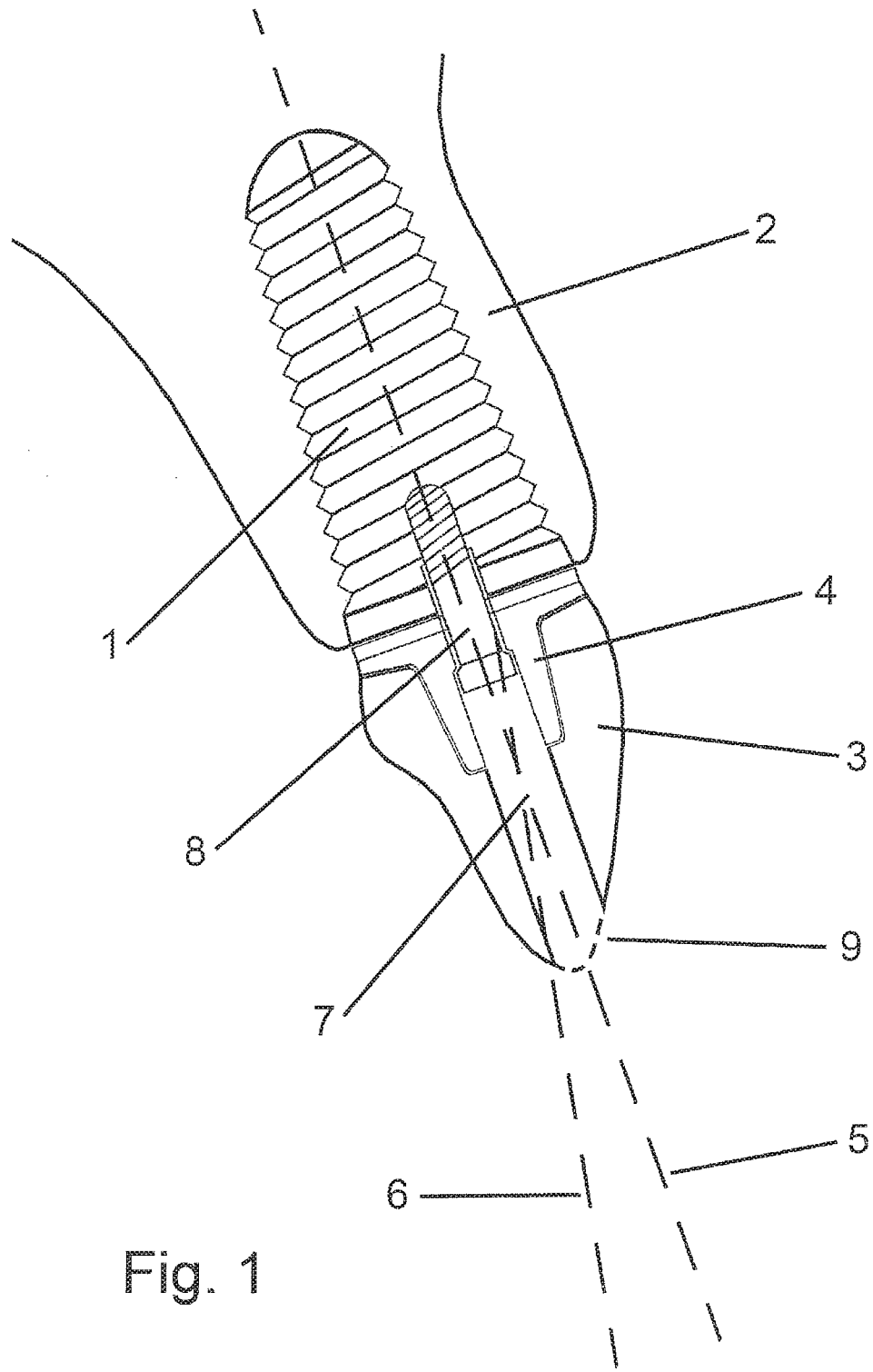

(51) Int. Cl.
*A61C 13/08* (2006.01)
*A61C 5/70* (2017.01)

(52) U.S. Cl.
CPC ........ *A61C 8/0089* (2013.01); *A61C 13/0004* (2013.01); *A61C 13/0022* (2013.01); *A61C 13/081* (2013.01); *A61C 5/70* (2017.02)

(58) Field of Classification Search
CPC ..... A61C 13/081; A61C 13/0022; A61C 5/08; A61C 8/005; A61C 8/006
USPC .......................................................... 433/173
See application file for complete search history.

(56) References Cited

U.S. PATENT DOCUMENTS

| | | | | |
|---|---|---|---|---|
| 5,702,346 | A * | 12/1997 | Lazzara | A61C 8/0022 433/173 |
| 5,873,721 | A * | 2/1999 | Willoughby | A61C 8/0001 433/172 |
| 5,947,733 | A * | 9/1999 | Sutter | A61C 8/005 433/173 |
| 7,108,511 | B1 * | 9/2006 | Shatkin | A61C 1/084 433/174 |
| 7,798,812 | B2 * | 9/2010 | Last-Pollak | A61C 8/0048 433/169 |
| 8,784,103 | B2 * | 7/2014 | Studer | A61C 8/005 433/172 |
| 9,039,415 | B2 * | 5/2015 | Streff | A61C 8/005 433/173 |
| 2002/0168613 | A1 * | 11/2002 | Riley | A61C 1/181 433/131 |
| 2011/0097688 | A1 * | 4/2011 | Rebaudi | A61C 8/0018 433/174 |

FOREIGN PATENT DOCUMENTS

| | | | | |
|---|---|---|---|---|
| KR | 20010091658 A | * | 10/2001 | ........... A61C 8/0068 |
| WO | 2012126475 A1 | | 9/2012 | |
| WO | 2013050796 A1 | | 4/2013 | |
| WO | 2013004387 A1 | | 10/2013 | |

* cited by examiner

PRIOR ART

DENTAL RESTORATION

CROSS-REFERENCE TO RELATED APPLICATIONS

This application is a National Stage application of International Patent Application No. PCT/EP2014/06871 filed on Jul. 23, 2014, which claims priority to German Patent Application No. 10 2013 014 660.7 filed on Sep. 3, 2013, the disclosures of which are incorporated herein by reference in their entirety.

The invention concerns a dental restoration, including an implant, abutment and supraconstruction as well as a process for maintaining and/or restoring a dental restoration which includes an implant, an abutment, and a supraconstruction.

Dental restorations, as are discussed here, are typically provided with a base consisting of an implant in combination with an abutment, as well as a supraconstruction which is fixed to the base. The abutments can be manufactured individually, for instance with the help of machining processes, or can be pre-fabricated. The supraconstruction typically consists of a dental ceramics material, for example of lithium disilicate or an oxide ceramics material, wherein lithium disilicate or other silicate ceramics materials may, for instance, be milled with the help of CAD/CAM processes.

It has also been suggested to manufacture a positive model of the supraconstruction out of a plastics material which can be removed without leaving residues, then embed it in a manner known per se and burn it out and fill the negative mould thus created with a pressed ceramics material.

The supraconstructions are connected with the base either detachably or non-detachably with many dental restorations as have already been put into practice.

In case of non-detachable connections, the abutment is typically fixedly screwed to the implant and then the supraconstruction, which is, for example, made out of a whole piece, i.e. milled, is glued on in such a fashion that a suitable adhesive gap is left. In the case of the detachable supraconstructions, a suitable access channel has to be created which may extend in the extension of the screw axis. Through said channel, the abutment screw of the screw connection can be introduced and removed.

With incisors, the root axis—and accordingly the implant axis as well usually—intersects the supraconstruction at the labial side if a straight access channel has been put into practice. The opening of the access channel is therefore also positioned on the labial side of the supraconstruction in a rather unattractive fashion, and it is typically visible also if suitably closed.

In order to face this problem, curved access channels have also been suggested, and have become known in numerous versions meanwhile. For example, a curved access channel has become known from EP 2 452 650 A1 which may even be curved in S-shape. FIG. 2b of this pre-publication shows that the access channel may then terminate at the lingual side of the supraconstruction, namely of the incisor there. This access channel can, for instance, be closed with the help of a light-curing PMMA, wherein typically, due to the differences in materials there, such in this fashion an irritational obstacle is created, such that the tongue of the patient tends to be irritated there.

Due to the curvature of the access channel, it is necessary to select a rather large diameter in order to be able to guide through the abutment screw.

It has also been suggested already to have the implant axis run slightly slanted towards the axis of the angle, for which purpose reference is to be made, for instance, to company Southern Implants, Eningen, Germany. With incisors, the implant axis can herewith be slanted by approximately 10° with relation the root axis, such that it has a slightly steeper course with relation to the occlusal plane—however, still not yet a vertical one. This solution, on the other hand, also has different disadvantages.

Therefore, the invention is based on the task of creating a dental restoration as well as a process in accordance with the attached claims, which create a reduced or even very distinctly reduced irritational obstacle for the tongue of a patient, without the necessity of making aesthetical compromises.

The dental restoration in accordance with the invention has the particular advantage that first a detachable supraconstruction is provided. Studies (Papaspyridakos P, Chen Cj, Chuang SK, Weber HP, Gallucci GO. "A systematic review of biologic and technical complications with fixed implant rehabilitations for edentulous patients.", Int J Oral Maxillofac Implants 2012; 27:102-110.) have resulted in that after ten years of wear time, about 60% of all dental restorations based on implants have at least been damaged and need at least partial exchange. With non-detachable supraconstructions, this leads to significant dental technological and dentist works which are perceived also by the patient as unpleasant.

In accordance with the invention, in contrast to this, the supraconstruction is designed to be detachable, which is in a particular manner. The access channel is put into practice in such a fashion that it terminates at a lingual or palatinal side, respectively, of the supraconstruction. Its opening towards the oral cavity, however, is minimised for the diameter is distinctly smaller than the screw head and just so thick that a minimised tool can be guided through there. The surface of the opening can amount, compared with the state of the art, as is, for example, visible from the above-mentioned EP 2 452 650 A1, to a third or even a fourth, such that—provided a flush realisation of the plug—it is not perceivable any more sensorially lingually.

In accordance with the invention, therefore, in spite of aesthetically extremely satisfactory results, the disadvantageous irritational obstacle with the state of the art can be removed.

In accordance with the invention, the loosening of the dental restoration for the purpose of repair is then done in that the plug which may consist of PMMA, ceramics or dental cement is simply removed—for instance by means of drilling out—so that then, with the help of a suitable tool, the abutment screw is loosened only slightly—without being removed.

As a result, the connection between the abutment and the implant is loosened, but the screw remains captured inside the supraconstruction and inside the abutment, and the combination of these two parts is simply taken out of the mouth of the patient.

Extracorporally, the suitable repair measures are then performed. Of course, it is also possible, for instance by means of heat treatment, to dissolve the adhesive glue used and remove it if this makes sense for the repair.

The repaired combination of supraconstruction and abutment can then be inserted into the mouth of the patient again without any thermal impairment to the patient, and the abutment screw can be fastened again in the same manner in reverse order and will lock the abutment and thus the supraconstruction to the implant. After removing the tool, which is for example provided as a screw driver, the access opening is then closed again with a new plug which has, for instance, been light-cured and closes in a precisely flush manner the oral cavity opening, for example, if necessary, by means of a finishing process, such as grinding.

It is to be understood that the solution in accordance with the invention is not restricted to the field of incisors. In the field of molars, for example, the opening can very well be positioned in the occlusal surfaces of the molars, for instance in the region of fissures and fossae, or in an occlusal marginal region, but in any case outside of cusp structures. As a result of the very small diameter of, for example, 0.8 mm, here as well the plug used cannot be perceived sensorially lingually.

In accordance with the invention, the slanting angle between the access channel in the region of the opening and the screw axis can be largely adapted to the requirements. Such, for example, with a curved access channel, an angle of between 0° and 40° can be put into practice without any problems.

A curved access channel, which is preferably provided with a constant radius and a constant degree of curvature over its extension, can be operated with the help of a screw driver with flexible shaft, or alternatively with the help of a screw driver with a gear-like drive unit.

In accordance with the invention, it is particularly favourable if the curved access channel is put into practice with the help of the manufacturing technology described above. For instance, by means of selective laser sintering, or, however, also by means of CAD grinding or drilling, respectively, a positive model of the supraconstruction is provided. This is embedded and the positive model is removed with the help of a heat treatment without any residues being left. The cavity thus remaining is filled with a pressed ceramics material which, when fired, constitutes the supraconstruction.

Alternatively, a straight access channel can also be employed at a corresponding slanting angle, which may extend up to an angle of approximately 30° with relation to the abutment screw axis. As a tool, a spherical-head Allen key or a spherical-head Torx key is then employed, and by means of slanting the implant axis in relation to the root axis, a further 10° of angular correction can be gained, such that in total also with a slanting angle of 40° of the root axis in relation to the vertical to the occlusal surface the desired offset of the opening at a lingual or palatinal surface, respectively, of the supraconstruction is successful.

This solution is also suitable for the realisation of milled ceramics, since then the access channel can be manufactured with the corresponding necessary dimensional accuracy, for instance by means of a precise drilling.

In accordance with the invention, it is also favourable that the solution in accordance with the invention can be put into practice independently of the connection type of the implant body, such as a hexagon socket, or an external hexagon connection, such that also different abutments fitting to the implants may be used in accordance with the invention.

Figure 2:
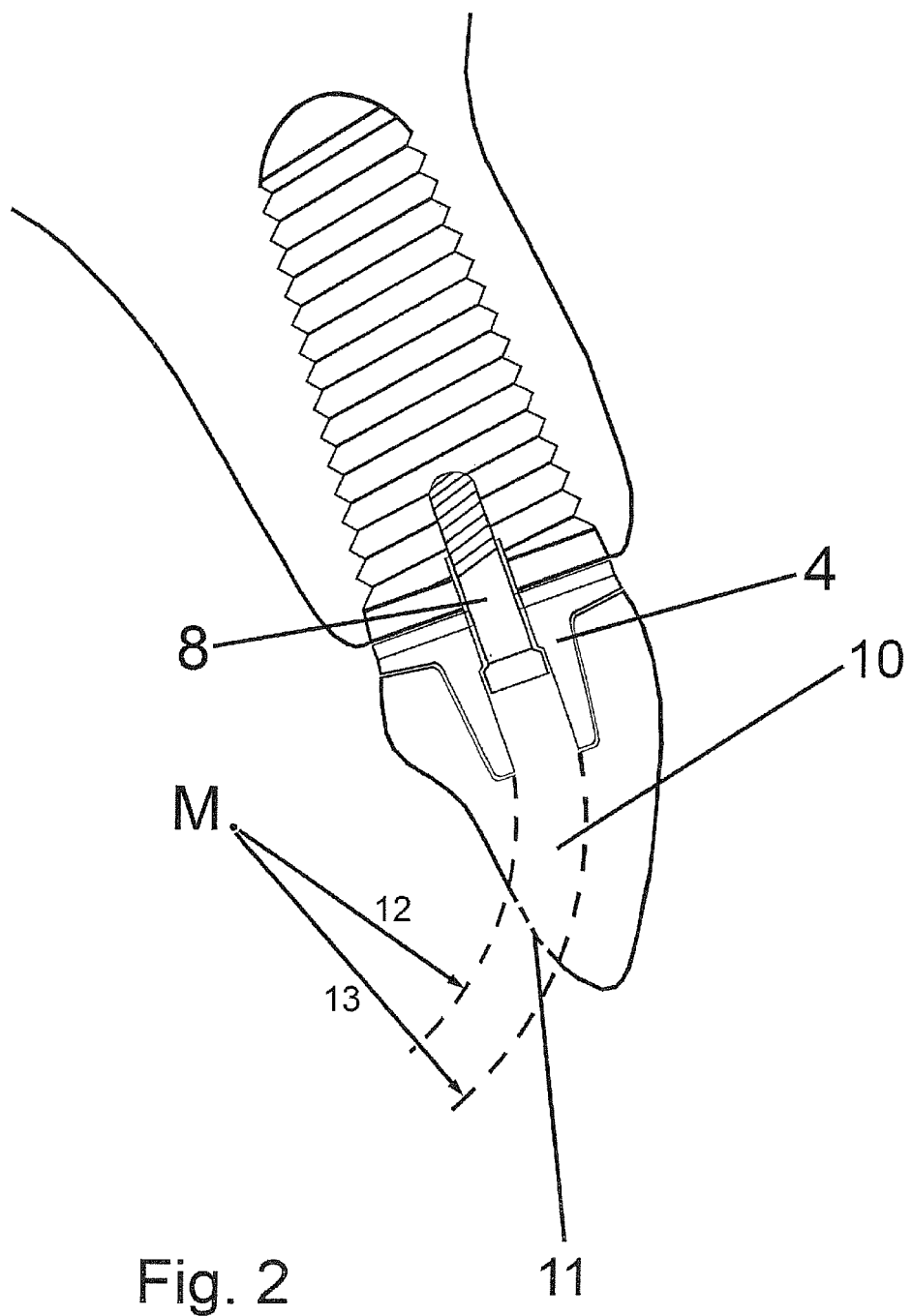
Figure 3:
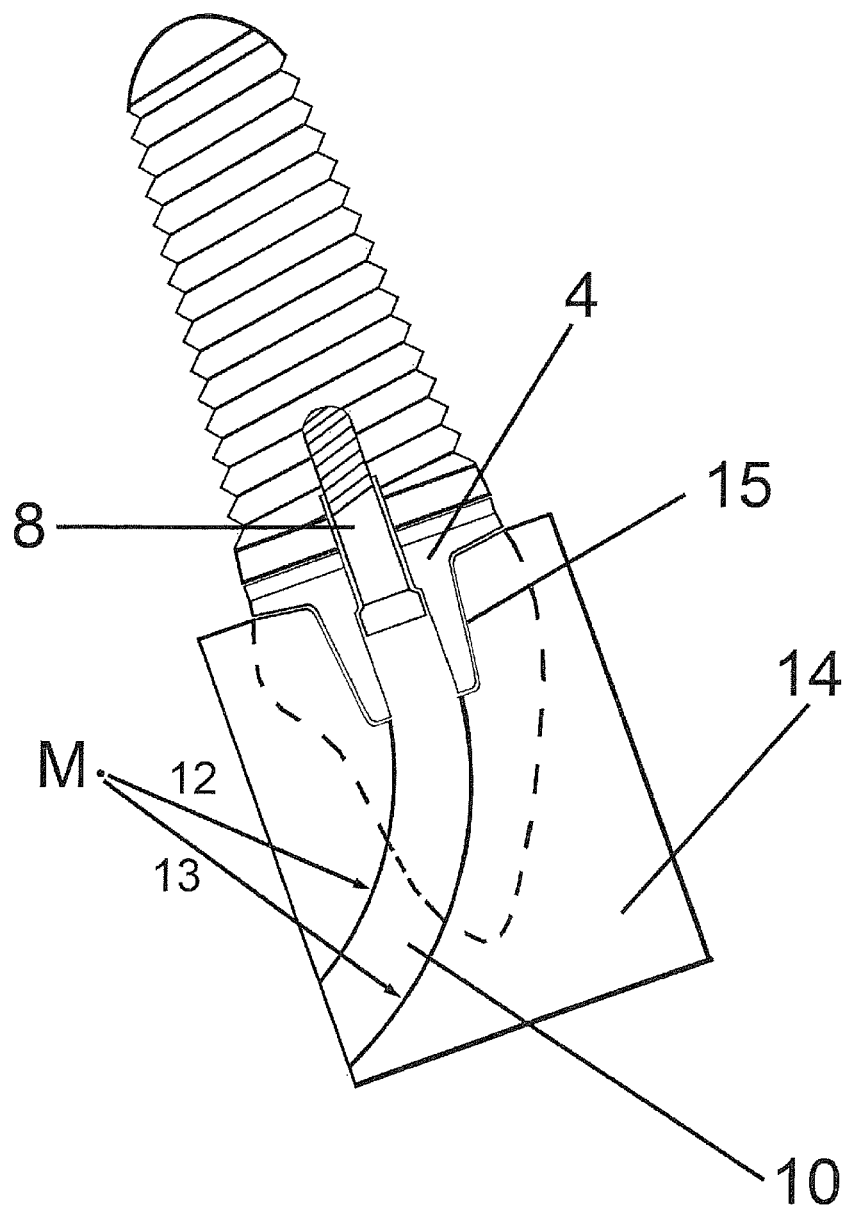
Figure 4:
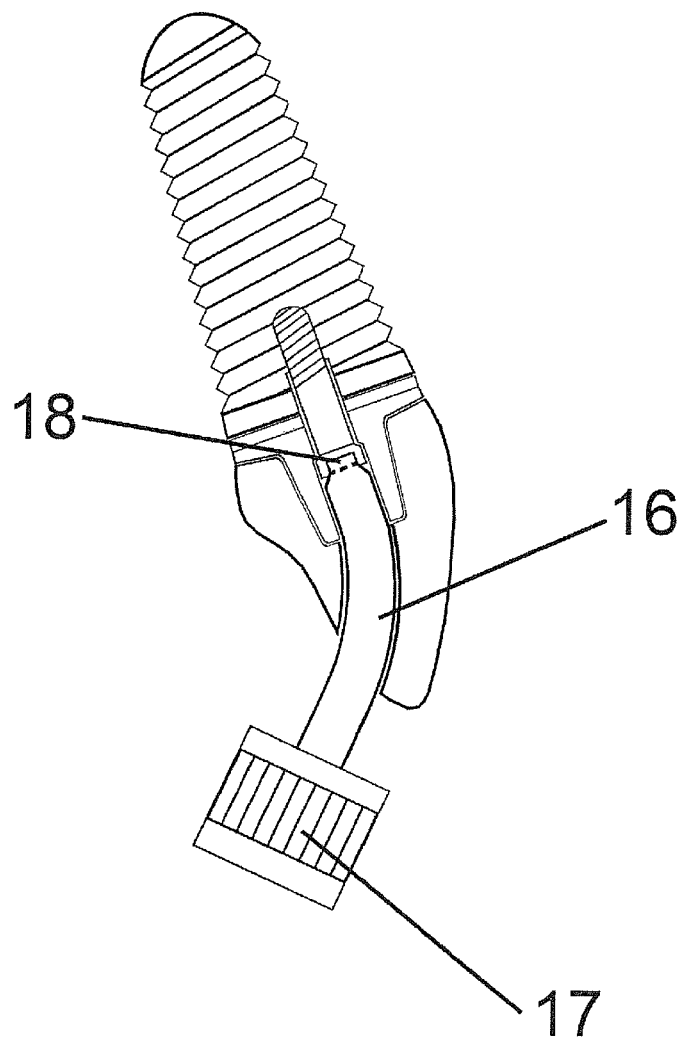
Figure 5:
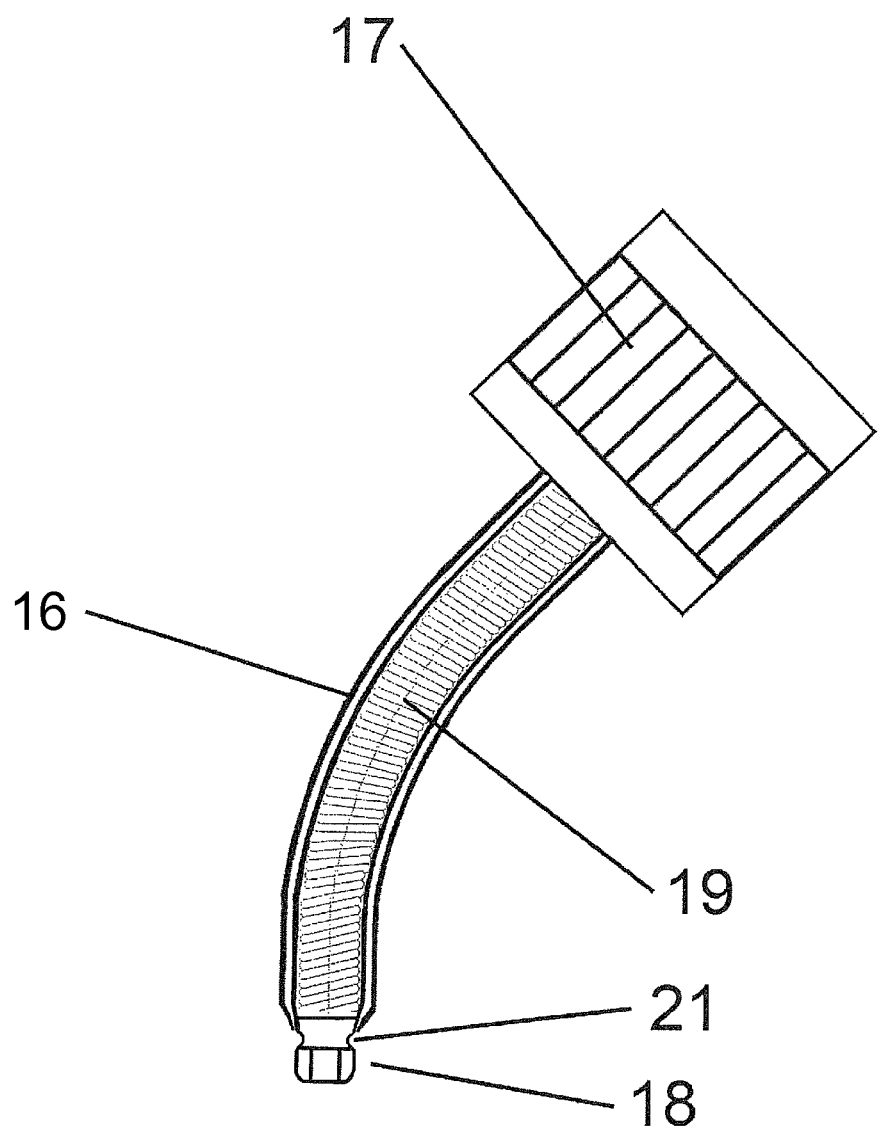
Figure 6:
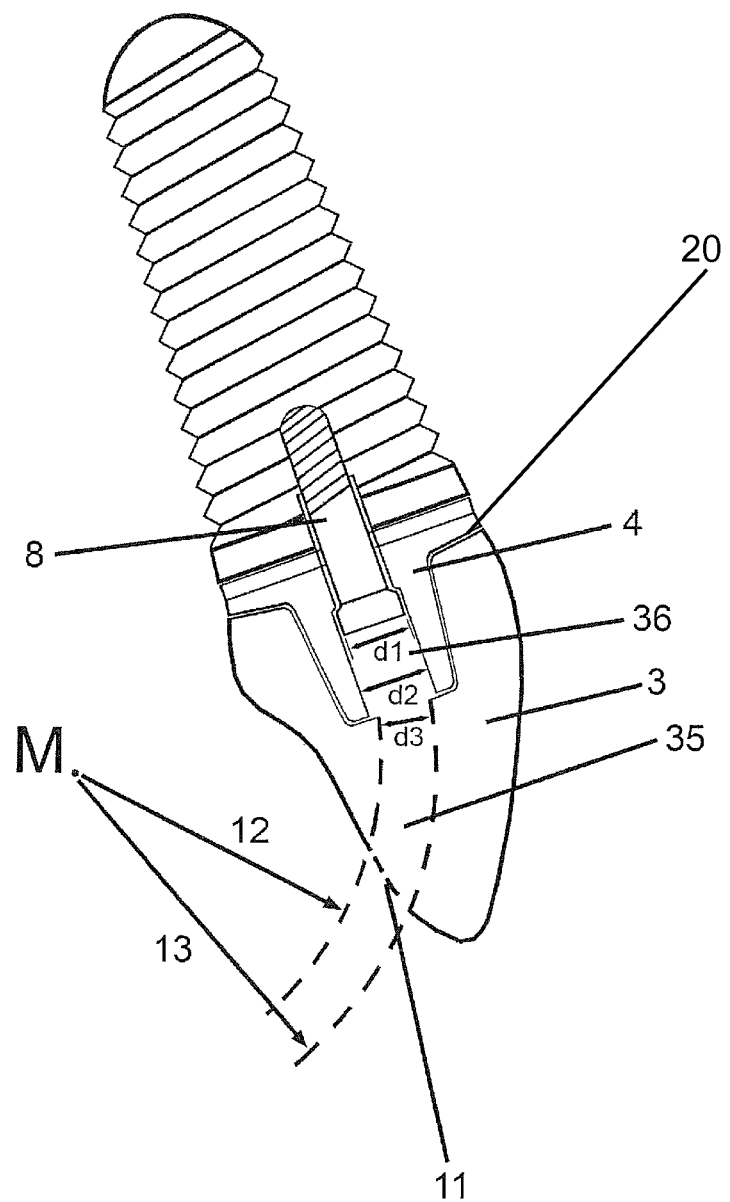
Figure 7:
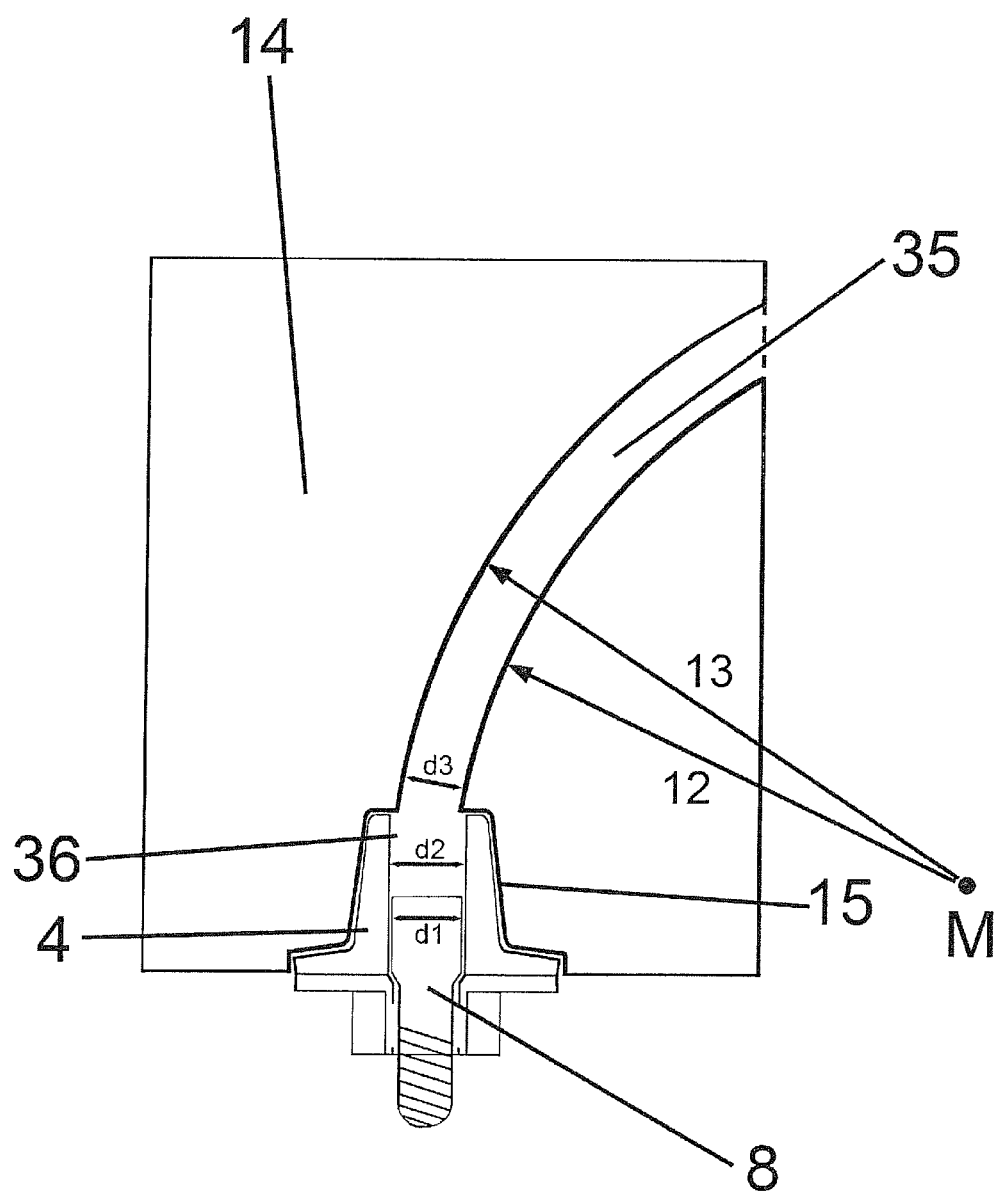
Figure 8:
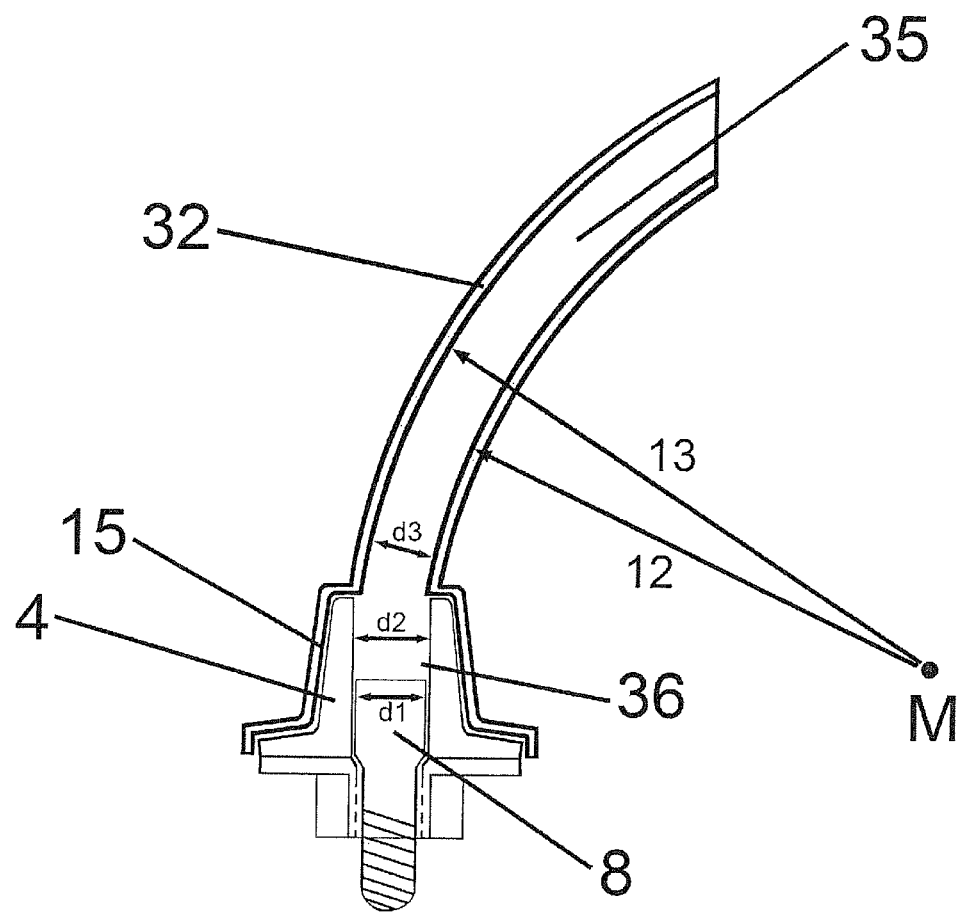
Figure 9:
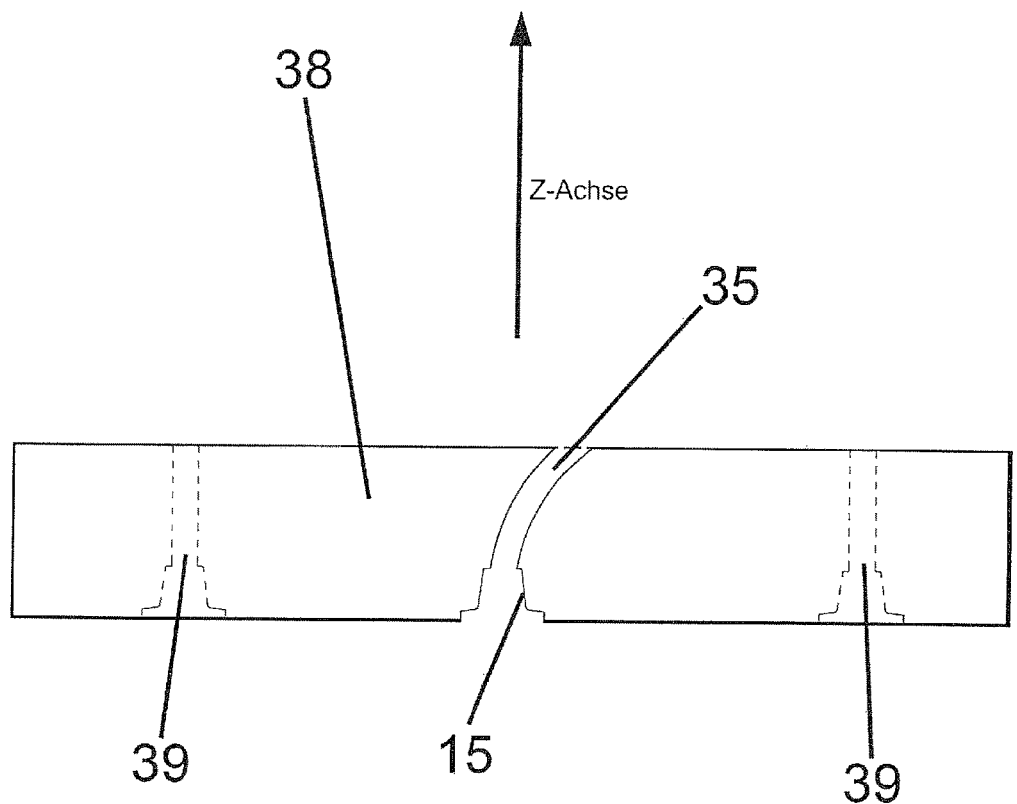

Further details, advantages, and features result from the subsequent description of a number of exemplary embodiments of the invention with the help of the drawings, which show:

FIG. 1 a dental restoration in accordance with the state of the art in a schematic sectional view;

FIG. 2 a dental restoration in accordance with the invention in a schematic sectional view;

FIG. 3 a block manufactured in accordance with the invention, for providing a supraconstruction of a dental restoration in accordance with the invention in one embodiment;

FIG. 4 a depiction of a dental restoration in accordance with the invention in a schematic shape, wherein also a tool in the form of a screw driver is depicted;

FIG. 5 a partial view of the tool in accordance with FIG. 4;

FIG. 6 a depiction of another embodiment of a dental restoration in accordance with the invention;

FIG. 7 a detailed view on the embodiment in accordance with FIG. 6;

FIG. 8 an embodiment of a modelling aid for the embodiment in accordance with FIGS. 6 and 7; and FIG. 9 a cross-sectional view of a blank for providing a supraconstruction in accordance with the invention.

From FIG. 1, a dental restoration in accordance with the state of the art is visible. For providing a denture in the area of the incisors, an implant 1 is provided which can be screwed in an upper-jaw bone 2 in a manner known per se.

A supraconstruction 3 is shaped as an incisor dental ceramics in the exemplary embodiment depicted. It has been glued onto an abutment 4. Abutment 4 has been connected with the implant with the help of an abutment screw 8, and has insofar been fixed. In this, between abutment 4 and supraconstruction 3, a not depicted adhesive joint is provided which accommodates a suitable dental cement for providing an adhesive bond.

Abutment screw 8 forms a screw axis 5 which extends through supraconstruction 3 in the incisal region. This screw axis 5 is oriented slightly slanted with relation to the root axis or dental-crown axis 6, since implant 1 is fixed with regards to its orientation in view of the present construction of upper-jaw bone 2.

Via a straight access channel 7, abutment screw 8 may be inserted, tightened and removed again, if necessary.

In this embodiment in accordance with the state of the art, access channel 7 must either be entirely filled or at least in the region of its opening 9, typically with a plastics material. The plastics material is softer than the dental ceramics of supraconstruction 3, and in addition is visible since it is partly provided also in the labial region.

From FIG. 2, it is visible in what fashion an access channel 10 in accordance with the invention can be put into practice in an alternative manner. Access channel 10 is curved at a constant curvature radius. Inside radius 12 of access channel 10 extends around a centre M2, while outside radius 13 extends around a centre M1, such that insofar a slight widening of access channel 10 is intended. This, however, is minimal, for example by 2% of the diameter, and it is possible just as well to have points M1 and M2 coincide, such that concentric segments are realised through radii 12 and 13.

From FIG. 3, access channel 10 is manufactured inside the supraconstruction, which is still present as a part of a block 14 in the exemplary embodiment depicted, i.e. before the shape of the incisor is manufactured by means of milling or the like. In the lower region at 15, a profiling is intended which corresponds exactly to the outside diameter and the outside profile of the associated abutment.

As a result of the minimally conical access channel 10, the removal during manufacturing is slightly facilitated.

From FIG. 4, it is visible in what fashion a dental restoration with abutment screw 8 in accordance with the invention can be put into practice. Abutment screw 8 is to be actuated through access channel 10, wherein the diameter of access channel 10—even this does not become very clear from FIG. 3—is distinctly smaller than the diameter of the head of abutment screw 8. A tool is shaped as a screw driver and is provided with a shank 16 and a gripping manubrium 17. Shank 16 is provided with a flexible shaft (compare FIG. 2). At its tip, shank 16 terminates in a screw profile 18. Screw profile 18 is adapted to the screw-profile geometry of abutment screw 8 and can, for instance, have the shapes of Allen, Torx, Pozidriv, octagon, or others.

From FIG. 5, it is visible in what fashion flexible shaft 19 extends through the shank of the screw driver. In a manner known per se, flexible shaft 19 makes possible an actuation, i.e. the exertion of a torque on screw profile 18, despite the curvature of shank 16.

As is visible from FIG. 5, a necking 21 is provided between screw profile 18 and flexible shaft 19, which necking 21 is provided circumferentially, and also makes possible a slightly slanted positioning of the screw profile in the screw profile of abutment screw 8.

In accordance with the exemplary embodiment depicted here of the tool, shank 16 is flexible. Alternatively, it is also possible to work with a solid, circular-arc shaped shank which, if applicable, is suitable for the transmission of even larger torques. In this case, it must be made sure that the abutment screw remains engaged, with its screw profile, with the screw profile of the tool during the entire process of screwing, wherein for guaranteeing this measure, both screw profiles may be extended in the axial direction of the screw, for the sake of simplicity. Alternatively, merely the last short partial region of shank 16 may be provided to be flexible as well, such that the shank can also be straightly aligned in this region when the screw is tightened.

From FIG. 8, a modelling aid 32 is visible, which serves for the purpose of manufacturing the screw channel with the help of a positive model in the lost-wax technique. Modelling aid 32 is accordingly provided with a curved channel 35 and a connection geometry 15 for providing an adhesive base for the abutment. Here, inside radius and outside radius are selected to be concentric, and the diameter of channel 35 results from the difference of both radii 12 and 13.

From FIG. 6, a further embodiment of a dental restoration in accordance with the invention is visible. In the sagittal cut, access channel 10 extends with a constant diameter D3. A chimney 36 of abutment 4 is provided with a diameter D2 which is somewhat larger than diameter D1 of the head of abutment screw 8. There is the relationship: D3<D1<D2, wherein the difference between D1 and D2 corresponds to the necessary minimum clearance for the screwability of abutment screw 8. As shown in FIG. 6, the chimney in the abutment is configured to receive the screw head and the screw head is able to be moved up and down in the chimney opening in the abutment.

For mounting the dental restoration in accordance with the invention, abutment 4 is first screwed into implant 1 with the help of abutment screw 8, and is safely attached there. Then, a suitable glue is applied, such as a dental cement, wherein an adhesive gap 20 is provided with an equal thickness over its extension.

Supraconstruction 3 is then glued onto abutment 4. Either before this is done, or also after gluing has been accomplished, access channel 7 is closed with the help of a PMMA plug in the region of opening 11. Said is cured by means of light curing, and is ground such that it is flush.

In an alternative, preferred embodiment, it is intended to put into practice, instead of the PMMA plug, a ceramics plug or said made out of dental cement, which is applied extracorporally. Herewith, tongue-irritational obstacles resulting from the PMMA plug can be further reduced.

Even if diameter D3 is depicted comparatively large in FIG. 6, it is to be understood that in practice it can also be kept distinctly smaller and makes necessary only the feed-through of the shank of a suitable tool.

From FIG. 7, it is newly visible how access channel 35 can also be put into practice already when producing a block 14 for the provision of the supraconstruction there.

From FIG. 8, it is visible in turn how a modelling aid 32 suitable for this can be employed in order to make possible the precise shape of access channel 35 in the lost-wax technique.

By way of example, a machinable, i.e. subtractively process able blank 38 is visible from FIG. 9. Said is, in the exemplary embodiment depicted, shaped as a flat cylinder, and is destined for the provision of a number of supraconstructions for dental restorations.

Before the supraconstruction itself is milled out with the help of CAD/CAM, each provided access channel 35 and 39, respectively, is created. This solution is also suitable for dental restorations comprising a number of segments with which a number of access channels for the corresponding abutment teeth extend through blank 38. Alternatively, straight access channels 39 can also be produced with the help of CAD/CAM.

The invention claimed is:

1. Dental restoration, comprising
   a base which comprises
      an implant (1) in combination with
      an abutment (4), having a chimney opening, and
   a supraconstruction (3) which is fixed to the abutment by adhesive bonding,
   wherein the base further comprises a screw having a threaded shank and a screw head, the screw head extends into the chimney opening of the abutment and connects the abutment to the implant so as to be fixed against rotation,
   said supraconstruction has an access channel (10) aligned with the abutment chimney opening for accessing the screw (8), an opening of the access channel is offset with respect to an extension of an axis of the screw in the lingual or palatinal direction, of the supraconstruction (3),
   wherein a diameter of the access channel is smaller than a diameter of the screw head of the screw (8), and the screw (8) can be screwed in and screwed out of the implant through the access channel (10),
   wherein the chimney opening of the abutment is configured to receive the screw head, and
   wherein the screw head can be moved up and down in the chimney opening of the abutment.

2. Dental restoration in accordance with claim 1, characterised in that the access channel extends in bow shape and extends between the screw head of the screw and a lingual or palatinal surface, of the supraconstruction (3).

3. Dental restoration in accordance with claim 1, characterised in that the access channel (10) has the same radius throughout the access channel.

4. Dental restoration in accordance with claim 1, characterised in that the opening of the access channel (10) is provided with a first cross-sectional area at the lingual or palatinal surface, of the supraconstruction (3) with a size as large as a second cross section of the access channel at positions other than a region of the opening.

5. Dental restoration in accordance with claim 1, characterised in that an axis of the access channel (10) extends slanted, at an angle of between 1° and 45° towards the lingual or palatinal surface of the supraconstruction (3) and the opening is provided in elliptical shape.

6. Dental restoration in accordance with claim 5, wherein the angle of the access channel is between 5° and 30° towards the lingual or palatinal surface of the supraconstruction (3) and the opening is provided in elliptical shape.

7. Dental restoration in accordance with claim 5, wherein the angle of the access channel is between 10° and 20° towards the lingual or palatinal surface of the supraconstruction (3) and the opening is provided in elliptical shape.

8. Dental restoration in accordance with claim 5, wherein the angle of the access channel is approximately 15° towards the lingual or palatinal surface of the supraconstruction (3) and the opening is provided in elliptical shape.

9. Dental restoration in accordance with claim 1, characterised in that the extension of the screw axis (5) intersects a vestibular surface of the supraconstruction (3) and the screw axis and the axis of the access channel (10) diverge from each other at an angle of 1° to 45°.

10. Dental restoration in accordance with claim 9, wherein the angle of divergence is between 5° and 30°.

11. Dental restoration in accordance with claim 9, wherein the angle of divergence is between 10° and 20°.

12. Dental restoration in accordance with claim 9, wherein the angle of divergence is 15°.

13. Dental restoration in accordance with claim 1, characterised in that the supraconstruction (3) is provided as an incisor or cuspid suprastructure and the opening extends at the lingual or palatinal side of the suprastructure from a cervical to an incisal end, and that the distance of the incisal end from the incisal surface of the suprastructure amounts to maximally double, the distance between the incisal and the cervical end of the opening.

14. Dental restoration in accordance with claim 1, characterised in that the opening is shaped during the forming of the supraconstruction (3) as a molar or pre-molar supraconstruction (3) adjoining a cusp structure of an occlusal surface, spaced apart from the base of the cusp by at least 0.5 mm.

15. Dental restoration in accordance with claim 1, characterised in that the screw head is provided with a screw profile selected from the group consisting of a Pozidriv profile, an Allen profile, and a Torx profile and the diameter of the access channel is slightly, by maximally 10%, larger than the diameter of the screw profile at the screw-head side end of the access channel (10).

16. Dental restoration in accordance with claim 15, wherein the diameter of the access channel is slightly larger, by 5%, than the diameter of the screw profile at the screw-head side end of the access channel (10).

17. Dental restoration in accordance with claim 1, characterised in that the screw profile is provided as an Allen profile or as a Torx profile which ends concavely, in a spherical-segment shaped at the screw side and is shaped for supporting a spherical-head Allen tool or Torx tool, and that the access channel extends in a straight fashion through the suprastructure in a diameter corresponding to the diameter of the screw profile.

18. Dental restoration in accordance with claim 1, characterised in that the angle between the screw axis (5) and the access channel axis is individually adapted to the patient specifications and is set in such that with an incisal or cuspid supraconstruction (3) the opening of the access channel (10) at the lingual or palatinal surface, adjoins the incisal surface or is spaced apart from said incisal surface by no greater than 1 mm.

19. Dental restoration in accordance with claim 1, characterised in that the supraconstruction (3) is provided with an adhesive surface which faces towards an abutment (4) and/or implant (1), wherein the adhesive gap extends exclusively between the supraconstruction (3) and the abutment (4).

20. Dental restoration in accordance with claim 1, further including a screw driver provided with a flexible shaft (19) which forms a shank (16) and that the side of the access channel (10) with a largest radius is provided as a guiding surface for the shank (16).

21. Dental restoration in accordance with claim 20, wherein the diameter of the access channel is slightly larger by 7% and 20% than the diameter of the screw driver shank.

22. Dental restoration in accordance with claim 20, wherein the diameter of the access channel is slightly larger by between 10% and 15% larger than the diameter of the screw driver shank.

23. Dental restoration in accordance with claim 1, characterised in that the dental restoration is intended for a side tooth in the lower jaw, at which the root axis or the implant axis penetrates the lingual side or the palatinal side of the supraconstruction (3) and that the access channel (10) is offset with respect to the root or implant axis in a buccal direction and ends at a fosae or fissure of the occlusal surface of the molar.

24. Process for maintaining and/or restoring a dental restoration which comprises
    an implant (1),
    an abutment (4), and
    a supraconstruction (3),
    wherein the abutment (4) comprises a chimney opening and is configured to receive and support a screw head of an implant screw,
    wherein the supraconstruction has an access channel (10) aligned with the abutment chimney opening for accessing the screw, the access channel extends starting from the screw head to a lingual surface of the supraconstruction (3), slanted towards the axis of the implant screw, wherein the screw head can be moved up and down in the chimney opening in the abutment,
    wherein a diameter of the screw head is larger than a diameter of the access channel (10, 35)
    said process comprising releasing the implant screw with the help of a screw driver,
    wherein the screw head is captured inside the chimney opening which extends between the abutment (4) and the supraconstruction (3), and
    after releasing the screw, the abutment (4) and supraconstruction (3) as a unit, is freely removable and removing the abutment and the supraconstruction unit,
    loosening and removing a bond between the abutment and supraconstruction unit, and
    providing a new or restored supraconstruction (3) for bonding to the abutment.

* * * * *